United States Patent
Moszner et al.

(10) Patent No.: US 10,533,025 B2
(45) Date of Patent: Jan. 14, 2020

(54) ACYL GERMANIUM PHOTOINITIATORS AND PROCESS FOR THE PREPARATION THEREOF

(71) Applicant: Ivoclar Vivadent AG, Schaan (LI)

(72) Inventors: Norbert Moszner, Mauren (LI); Iris Lamparth, Grabs (CH); Urs Karl Fischer, Arbon (CH); Harald Stüger, Graz (AT); Michael Haas, Graz (AT); Georg Gescheidt Demner, Graz (AT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 15/763,959

(22) PCT Filed: Sep. 26, 2016

(86) PCT No.: PCT/EP2016/072835
§ 371 (c)(1),
(2) Date: Mar. 28, 2018

(87) PCT Pub. No.: WO2017/055209
PCT Pub. Date: Apr. 6, 2017

(65) Prior Publication Data
US 2018/0265527 A1    Sep. 20, 2018

(30) Foreign Application Priority Data

Sep. 29, 2015 (EP) .................................. 15187284

(51) Int. Cl.
*C07F 7/30* (2006.01)
*C08F 2/50* (2006.01)
*C08F 4/72* (2006.01)

(52) U.S. Cl.
CPC .................. *C07F 7/30* (2013.01); *C08F 2/50* (2013.01); *C08F 4/72* (2013.01)

(58) Field of Classification Search
CPC ........ C08F 4/72; C08F 2/50; C08F 222/1006; C07F 7/30; A61K 6/0052
See application file for complete search history.

(56) References Cited

U.S. PATENT DOCUMENTS

| | | |
|---|---|---|
| 4,071,424 A | 1/1978 | Dart et al. |
| 4,457,818 A | 7/1984 | Denyer et al. |
| 4,525,256 A | 6/1985 | Martin |
| 6,043,361 A | 3/2000 | Evans et al. |
| 6,344,556 B1 | 2/2002 | Evans et al. |
| 6,479,592 B2 | 11/2002 | Rheinberger et al. |
| 7,365,222 B2 | 4/2008 | Moszner et al. |
| 7,605,190 B2* | 10/2009 | Moszner ............... A61K 6/083 522/105 |
| 8,829,067 B2* | 9/2014 | Moszner .............. A61K 6/0017 522/66 |
| 10,342,744 B2* | 7/2019 | Moszner |
| 2003/0021565 A1 | 1/2003 | Khudyakov et al. |
| 2008/0076847 A1* | 3/2008 | Moszner ............... A61K 6/0017 522/26 |
| 2015/0080490 A1* | 3/2015 | Burtscher ............ A61K 6/0835 522/18 |
| 2016/0357031 A1* | 12/2016 | Holland .......... B29D 11/00038 |
| 2018/0036209 A1* | 2/2018 | Moszner ................ C07C 233/58 |
| 2019/0167533 A1* | 6/2019 | Moszner ................. C08L 35/02 |

FOREIGN PATENT DOCUMENTS

| | | |
|---|---|---|
| CA | 2296227 A1 | 7/2000 |
| CA | 2397140 A1 | 7/2001 |
| CA | 2930267 A1 | 5/2015 |

OTHER PUBLICATIONS

International Preliminary Report on Patentability of PCT/EP2016/072835, dated Apr. 3, 2018, 7 pages.
Moszner, N. et al., "Photoinitiators for direct adhesive restorative materials," Research Signpost, pp. 93-114, 2010, Kerala, India.
Ganster, Beate et al., "New Photocleavable Structures. Diacylgermane-Based Photoinitiators for Visible Light Curing," Macromolecules, 41, pp. 2394-2400, 2008.
Moszner, Norbert et al., "Benzoyl germanium derivatives as novel visible light photoinitiators for dental materials," Dental Materials, 24, pp. 901-907, 2008.
Moszner, Norbert et al., "Benzoylgermanium Derivatives as Novel Visible-Light Photoinitiators for Dental Composites," Macromolecular Materials and Engineering, 294, pp. 877-886, 2009.
Fouassier, J. P., "Radiation Curing in Polymer Science and Technology—Photoinitiating Systems," Elsevier Applied Science, vol. II, London and New York, 1993.

\* cited by examiner

*Primary Examiner* — Sanza L. McClendon
(74) *Attorney, Agent, or Firm* — Ann M. Knab; Thad McMurray

(57) ABSTRACT

Acyl germanium compound according to general formula $[R_m Ar-(C=O)-]_4-Ge$ and process for the preparation thereof. The compound is suitable as initiator for radical polymerization.

10 Claims, No Drawings

ACYL GERMANIUM PHOTOINITIATORS AND PROCESS FOR THE PREPARATION THEREOF

CROSS-REFERENCE TO RELATED APPLICATIONS

This application is a National Stage application of International patent application PCT/EP2016/072835 filed on Sep. 26, 2016, which claims priority to European patent application No. 15187284.3 filed on Sep. 29, 2015, all the disclosures of which are incorporated herein by reference in their entirety.

FIELD OF THE INVENTION

The present invention relates to polymerizable compositions which contain an acyl germanium compound as polymerization initiator. The compositions are particularly suitable for the preparation of adhesives, coatings, cements, composites, shaped parts such as rods, plates, disks or lenses etc. and in particular dental materials.

The photoinitiator used plays a decisive role for the curing of photopolyreactive resins. Upon irradiation with UV or visible light it absorbs light and forms the polymerization-initiating species. In the event of radical polymerization these are free radicals. The photoinitiators are divided into two classes based on the chemical mechanism of radical formation.

Norrish type I photoinitiators form free radicals upon irradiation by unimolecular bond cleavage. Upon irradiation, Norrish type II photoinitiators undergo a bimolecular reaction wherein the photoinitiator in the excited state reacts with a second molecule, the coinitiator, and the polymerization-initiating radicals form by electron and proton transfer. Type I and type II photoinitiators are used for UV light curing; to date apart from bisacyldialkyl germanium compounds type II photoinitiators are almost exclusively used for the visible light range.

BACKGROUND OF THE INVENTION

UV curing is characterized by a high reaction rate and is frequently used for the coatings of different substrates such as e.g. wood, metal or glass. Thus for example in EP 1 247 843 A2 a UV-curing coating material is described, in which type I photoinitiators such as diethoxyphenylacetophenone or acyl- or bisacylphosphine oxide are used.

WO 01/51533 A1 describes a UV-curing wood-coating material in which acylphosphine oxides, α-hydroxyalkylphenones or α-dialkoxyacetophenones are also used as photoinitiators. Above all, transparent coatings with low layer thickness can be produced with UV curing due to the low wavelength of the UV light. The limits of UV curing are reached with pronounced shading or pigmentation and greater layer thicknesses. Such photopolyreactive resins with clearly reduced transparency cure only incompletely with UV light.

If greater through-curing depths are required, such as for example in the curing of light-curing dental filling materials, visible light is used for irradiation. The photoinitiator system most frequently used for this is a combination of an α-diketone with an amine coinitiator as described e.g. in GB 1 408 265.

Dental compositions in which this photoinitiator system is used are disclosed e.g. in U.S. Pat. Nos. 4,457,818 or 4,525,256, wherein preferably camphorquinone is used as α-diketone. Camphorquinone has an absorption maximum at a wavelength of 468 nm. As a result camphorquinone displays a strong yellow colouring with the disadvantage that materials initiated with camphorquinone/amine often have a yellow cast after curing, as the initiator system is not completely bleached. (N. Moszner, R. Liska, Photoinitiators for direct adhesive restorative materials, In: Basics and Applications of Photopolymerization Reactions, Vol. 1; Fouassier, J.-P., Allonas, X., Eds., Research Signpost, Kerala, 2010, 93-114). This bleaching behaviour is very disadvantageous in particular in the case of bright white shades of the fully polymerized material. In addition, when used in acid adhesives, camphorquinone amine systems have the disadvantage that the radical-forming amine component protonates and is thereby partially deactivated for radical formation.

The use of germanium compounds as photoinitiators is known. Bisacyldialkyl germanium compounds are above all efficient Norrish Type I photoinitiators for curing in the blue light range (B. Ganster, U. K. Fischer, N. Moszner, R. Liska, New photocleavable structures, Diacylgerman-based photoinitiators for visible light curing, Macromolecules 41 (2008) 2394-2400; N, Moszner, U. K. Fischer, B, Ganster, R. Liska, V, Rheinberger, Benzoyl germanium derivatives as novel visible light photoinitiators for dental materials Dent. Mater. 24 (2008) 901-907; N. Moszner, F. Zeuner, I. Lamparth, U. K. Fischer, Benzoylgermanium derivatives as novel visible-light photoinitiators for dental composites, Macromol. Mater. Eng. 294 (2009) 877-886).

EP 1 905 413 A1 and EP 1 905 415 A1 disclose mono-, bis- and triacyl germanium compounds which are suitable as photoinitiators for curing dental materials with visible light. Their synthesis is costly and is carried out starting from expensive dialkyl germanium dihalides using the dithiane protective-group technique and purification using column chromatography.

From EP 2 103 297 A1 suitable acyl germanium compounds which contain several germanium atoms are known as photoinitiators.

WO 2015/067815 A1 discloses bis (germyl)ketones with the formula $R^1R^2R^3Ge(CO)GeR^4R^5R^6$ and processes for the preparation thereof. These bis(germyl)ketones are also intended to be suitable as photoinitiators for dental materials.

SUMMARY OF THE INVENTION

The object of the invention is to provide photoinitiators for the visible range, which are characterized by improved reactivity and curing characteristics and which can be activated in particular by visible light in the long-wave range. A further object of the invention is to provide a simplified process for the preparation of acyl germanes.

DETAILED DESCRIPTION

This object is achieved by tetra- or tetrakis-acyl germanes corresponding to general formula (I):

$$[R_mAr-(C=O)-]_4-Ge \qquad (I)$$

in which the variables have the following meanings:
Ar a mono- or polycyclic hydrocarbon radical with 6 to 18 ring-carbon atoms, which can be substituted m times by the R group and which can contain one or more heteroatoms in the ring, wherein
m is an integer from 0 to 6 and cannot be greater than the number of substitutable hydrogen atoms in Ar, R is halogen, $NR^1{}_2$, OH, $OSiR^2{}_3$, $(C=O)R^3$, CN, $NO_2$, $CF_3$, $COOR^4$, a $C_1$ to $C_{20}$-alkyl, -alkenyl, -alkoxy or -alkenoxy radical, which can be linear, branched or cyclic, which can be interrupted by one or more O atoms and which can bear a radically polymerizable group, or =O, wherein $R^1$ to $R^3$ independently of each other are in each case H or a linear or branched $C_1$- to $C_{12}$-alkyl radical and $R^4$ is H, a linear or branched $C_1$- to $C_{12}$-alkyl radical or $SiR^5{}_3$, wherein $R^5$ is a linear or branched $C_1$ to $C_{10}$ alkyl radical.

If several R radicals are present (m>1), these can be different or preferably identical. Preferred radically polymerizable groups which can be present as substituents in the R radicals, are vinyl, styryl, acrylate ($CH_2=CH-CO-O-$), methacrylate ($CH_2=C(CH_3)-CO-O-$), acrylamide ($CH_2=CH-CO-NR^6-$ with $R_6=H$ or $C_1$-$C_8$-Alkyl), methacrylamide ($CH_2=C(CH_3)-CO-NH-$), particularly preferably (meth)acrylate, methacrylamide and/or N-alkylacrylamide. The R radical (s) preferably bear 0 to 3, in particular 0 to 1 radically polymerizable groups. In non-cyclic radicals the polymerizable groups are preferably arranged terminal.

According to the rules of chemical nomenclature, compounds in which Ar is an unsubstituted group are to be called tetraacyl germanes, while compounds in which Ar is substituted, must be called tetrakis(acyl)germanes. For the sake of simplicity, the term tetraacyl germanes is used here for both compound groups.

Ar is preferably a polycyclic hydrocarbon radical which contains at least one aromatic ring, particularly preferably an aromatic hydrocarbon radical. Preferred polycyclic hydrocarbon radicals with at least one aromatic ring are anthraquinone and naphthoquinone. In addition to the benzene radical, in particular condensed aromatic groups such as naphthalene, anthracene, phenanthrene and naphthacene groups are preferred as aromatic hydrocarbon radicals.

Ar can contain one or more, preferably 1 to 2 heteroatoms in the ring. Preferred heteroatoms are O, S and particularly preferably N. Particularly preferred heteroaromatic radicals are pyridine, pyrimidine and quinoline.

All stereoisomeric forms and mixtures of various stereoisomeric forms such as e.g. racemates are covered by Formula (I) and the other formulae shown herein. The formulae cover only those compounds that are compatible with the chemical valence theory. For example m cannot be greater them the number of substitutable hydrogen atoms in the Ar group. If R is bonded to Ar via two bonds, the maximum number of possible R radicals is correspondingly smaller.

The indication that a radical can be interrupted by a heteroatom such as O is to be understood to mean that the O atoms are inserted into the carbon chain or the carbon ring of the radical, i.e. are bordered on both sides by carbon atoms. The number of heteroatoms is therefore at least 1 fewer than the number of carbon atoms, and the heteroatoms cannot be terminal. In the case of hydrocarbon radicals which contain carbon atoms and heteroatoms, the number of heteroatoms is always less than the number of carbon atoms, without taking substituents into account.

Halogen (abbreviated to Hal) preferably stands for F, Cl, Br or I, in particular F, Cl, quite particularly preferably Cl.

Tetraacyl germanes corresponding to general formula (I) are particularly preferred, in which the variables have the following meanings:

Ar an aromatic $C_6$-$C_{10}$ radical, which can be substituted m times by R, wherein m is an integer from 1 to 3 and R is Cl, $NR^1{}_2$, $OSiR^2{}_3$, $(C=O)R^3$, CN, $NO_2$, $CF_3$, $COOR^4$, or a $C_1$ to $C_{10}$-alkyl, alkenyl, alkoxy or alkenoxy radical, which can be linear, branched or cyclic, which can be interrupted by one or more O atoms, and which can contain a radically polymerizable group, preferably vinyl, methacrylate, (meth)acrylamide or N-alkylacrylamide, wherein the radically polymerizable group in the case of non-cyclic radicals is preferably terminal, wherein $R^1$ to $R^3$ independently of each other are in each case H or a linear or branched $C_1$- to $C_8$-alkyl radical and $R^4$ is H, a linear or branched $C_1$- to $C_8$-alkyl radical or $SiR^5{}_3$ and $R^5$ is a linear or branched $C_1$ to $C_5$ alkyl radical.

Tetraacyl germanes according to general formula (I) are further preferred, in which the variables have the following meanings:

Ar a phenyl radical, pyridyl radical, naphthyl radical, anthryl radical, anthraquinonyl radical, which can be substituted m times by R, wherein m is an integer from 1 to 3 and R is $NR^1{}_2$, CN, $NO_2$, $CF_3$, a $C_1$- to $C_3$-alkyl radical or $C_1$ to $C_3$-alkoxy radical, which is preferably linear and which can bear a terminal radically polymerizable group, preferably vinyl, acrylate, methacrylate, wherein $R^1$ is H or a preferably linear $C_1$- to $C_3$-alkyl radical.

If Ar is a phenyl radical and m=1, the R radical is preferably located in the para-position relative to the yl position, if m=2 or 3, the R radicals are preferably located in the ortho-and para-position relative to the yl position. The preferred and particularly preferred meanings of the individual variables can be chosen independently of each other in each case.

Quite particularly preferred are compounds of Formula (I), in which Ar is a phenyl radical, which is substituted by R m times. m is preferably 1-3, particularly preferably 1, and R is preferably an electron donor group, in particular an alkoxy group.

According to the invention compounds of Formula (I) are preferred which have an absorption maximum at 400 nm to 700 nm, particularly preferably 400 to 550 nm, such as e.g. tetrabenzoyl germanium or tetra(4-methoxybenzoyl)germanium. The absorption spectrum of the compounds of Formula (I) can be adjusted in a targeted manner by the selection of the R group. For example $NO_2$ or CN substituents bring about a bathochromic shift of the absorption spectrum, i.e. compounds in which one or more of the R radicals are CN, adsorb light with a longer wave length, with the result that the polymerization can be initiated by visible light in the longer wave length range.

Tetraacyl germanes of general formula (I) are not known from the state of the art and cannot be prepared with conventional processes. These compounds are characterized by a high reactivity, i.e. an excellent polymerization-initiating effect and a good through-curing depth upon irradiation with visible light. This is of great advantage not only in the case of dental materials and in particular in the case of dental filling composites, but also in the case of non-dental uses.

It was surprisingly found that $(arylacyl)_k(alkyl)_{4-k}$germanes of Formula I' can be prepared by reacting (trialkylsilyl)germanes of Formula $(R'_3Si)_k GeR''_{4-k}$ (II) in the presence of a base and an arylacyl halide (III).

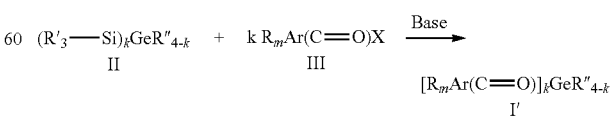

wherein:

R' is an alkyl group with 1 to 6, preferably 1 to 4 C atoms, particularly preferably $CH_3$, R" is an alkyl group with 1 to 12, preferably 1 to 6, particularly preferably 1 to 4 C atoms, quite particularly preferably CH$_3$, C$_2$H$_5$ or C$_4$H$_9$, X is F, Cl, Br or I, preferably F or Cl, k is an integer from 1 to 4 and R has the meaning given above.

In the case of R' and R" linear alkyl groups are preferred in all cases.

Alkali metal alcoholates, particularly preferably potassium tert-butylate, alkali metal amides, particularly preferably lithium diisopropylamide, or alkali metal organic compounds, particularly preferably n-butyllithium, are preferably used, as bases.

Preferred arylacyl halides of Formula III are derived directly from the preferred and particularly preferred definitions of the Ar and R groups. The following compounds are examples of this:

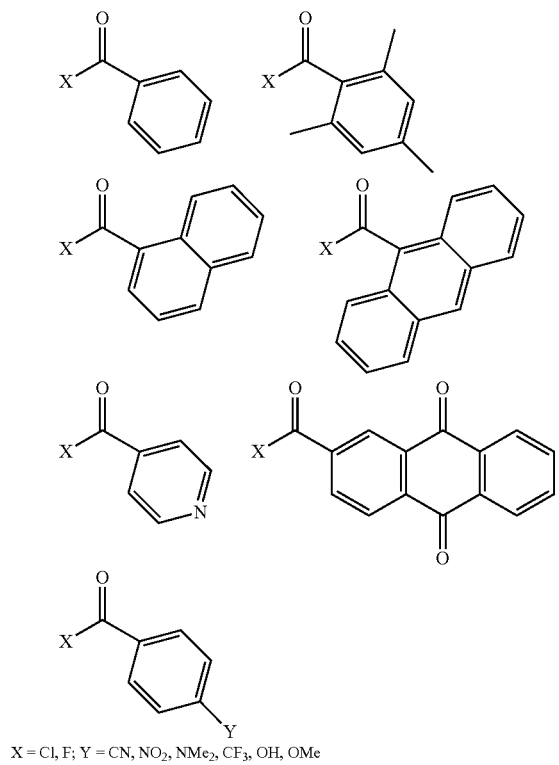

X = Cl, F; Y = CN, NO$_2$, NMe$_2$, CF$_3$, OH, OMe

Preferably, trimethylsilyl germane (R'3Si)$_k$GeR"$_{4-k}$ (II) is firstly reacted with the base to form (R'$_3$Si)$_{k-1}$R"$_{4-k}$GeM, wherein M is a metal ion, preferably an alkaline earth and in particular an alkali metal ion, and (R'$_3$Si)$_{k-1}$R"$_{4-k}$GeM is then converted with the acyl halide of Formula (III) into a compound of Formula (R'$_3$Si)$_{k-1}$R"$_{4-k}$Ge(C=O) ArR$_n$. In this way the (R'$_3$Si)-groups of Formula (II) are successively exchanged for —(C=O)ArR$_n$ radicals. The intermediate products (R'$_3$Si)$_{k-1}$R"$_{4-k}$GeM are preferably not isolated.

With the process according to the invention acyl germanes of Formula (I') can be prepared with a high purity and with good yields. A particular advantage is that the use of costly protective group technology, using sulphur-containing protective groups can be avoided. Sulphur-containing impurities can be removed from the products only with great difficulty, and even small traces of sulphur-containing radicals lead to an unpleasant odour of the end product.

The starting materials (R'$_3$Si)$_k$GeR"$_{4-k}$ (II) required for the synthesis of the acyl germanes of Formula (I') can preferably be prepared by reacting the corresponding germanium chlorides Cl$_k$GeR"$_{4-k}$ (IV) with a trialkylsilyl bromide of Formula R'$_3$SiBr or preferably a trialkylsilyl chloride of Formula R'$_3$SiCl (V):

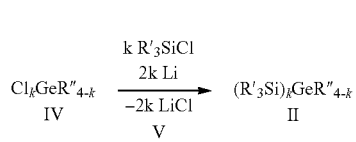

For this, R'$_3$SiBr or preferably R'$_3$SiCl (preferably 0.9 to 1.1 k, particularly preferably 0.99 k equivalents) is preferably first added to a suspension of finely dispersed Li (preferably 1.7 to 2.2 k, particularly preferably 1.85 k equivalents) in a suitable solvent, and a solution of the germanium chloride (preferably 1 equivalent) is then added slowly, An ether, particularly preferably THF is preferably used as solvent in each case. The quantity of solvent used is preferably 20 to 40 ml/g Li, quite particularly preferably 30 ml/g Li, or 1 to 5 ml/g GeCl$_4$, quite particularly preferably 2.5 ml/g GeCl$_4$. The reaction temperature is preferably +30 to −100° C., particularly preferably −78° C. The working up of the product mixture is preferably carried out by filtration, preferably through diatomaceous earth (Celite®), acid hydrolysis, preferably with a mixture of H$_2$SO$_4$/ice, phase separation and subsequent removal of the solvent, preferably by distillation. The products can advantageously be isolated by crystallization, sublimation or distillation.

According to a particularly preferred embodiment of the process according to the invention, acyl germanes of Formula (I') can be prepared by reacting trimethylsilyl germanes (Me$_3$Si)$_k$GeR"$_{4-k}$ (II') with potassium, tert-butylate (KOtBu) and then, reacting the intermediate with an acyl halide (III) (X=F or Cl):

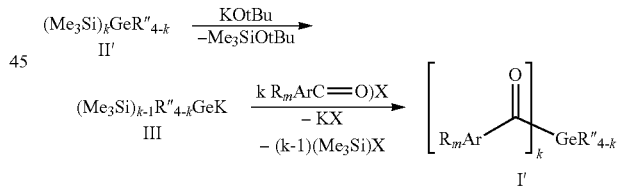

For forming (Me$_3$Si)$_{k-1}$R"$_{4-k}$GeK, (Me$_3$Si)$_k$GeR"$_{V-k}$ (preferably 1 equivalent) and KOtBu (preferably 0.9 to 4 equivalents, particularly preferably 1.1 equivalents) are preferably first dissolved in a suitable solvent and stirred until the reaction is completed. An ether is preferably used as solvent, particularly preferably DME (dimethoxyethane). The quantity of solvent used is preferably 10 to 60 ml/g KOtBu, particularly preferably 20 ml/g KOtBu. The reaction temperature is preferably +80 to −30° C., particularly preferably +25° C., the reaction time is preferably 0.5 to 3 hours, particularly preferably 1 hour.

The acyl halide (III) (preferably 1.0 to 1.5 equivalents) is then added and stirred until the reaction is complete, in order to obtain the acyl germane of Formula (I'). The acyl halide (III) can be used both as such and in solution, wherein the quantity of solvent is preferably 0 to 200 ml, particularly preferably 100 ml/mmol acyl halide. An ether, particularly preferably diethylether, is preferably used as solvent. The reaction temperature is preferably +30 to −100° C., quite particularly preferably −78° C., The reaction time is preferably 0.5 to 48 hours, particularly preferably 24 hours. The working up of the product mixture is preferably carried out by acid hydrolysis, preferably with a mixture of $H_2SO_4$/ice, phase separation and removal of the solvent e.g. by distillation. The product can be isolated by column chromatography and by crystallization, preferably only by crystallization.

Analogously, monoacyltrialkyl germanes, bisacyldialkyl germanes and trisacylmonoalkyl germanes can be produced directly and without protective group technology by reacting mono, bis-, tris- or tetra(trialkylsilyl)germanes of Formula (II) with acyl halides of Formula (III), Tetraacyl germanes of Formula (I') with k=4 are accessible by this process for the first time. For this, a trialkylsilyl germanium of Formula $(R'_3Si)_4Ge$ is reacted, in the presence of a base, with an aromatic aryl halide of Formula (III) in the manner described above. The trialkylsilyl germanium $(R'_3Si)_4Ge$ can be prepared as described by reacting germanium tetrachloride with $R'_3SiCl$ and metallic Li.

Tetraacyl germanes of Formula (I) can be prepared particularly advantageously as described above, by reacting tetrakis(trimethylsilyl)germanium $(Me_3Si)_4Ge$ with potassium tert-butylate (KOtBu) and then reacting with an acyl halide of Formula (III) (X=F or Cl):

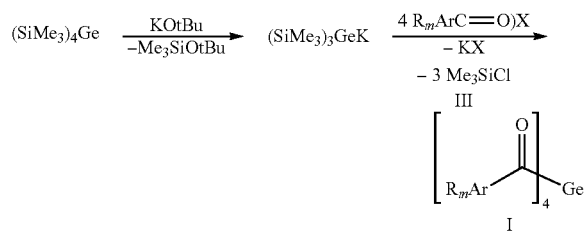

The acyl halide (III) is preferably added in a quantity of from 1.0 to 5 equivalents, particularly preferably 4.1 equivalents, and stirred until the reaction is complete. The acyl halide can be used as described both as such and in solution.

The tetraacyl germanes of general formula (I) and the $(acyl)_k(alkyl)_{4-k}$germanes of Formula (I') are particularly suitable as photoinitiators for polymerization, in particular as initiators for radical polymerization, photoaddition and for thiol-ene reaction (polyaddition). It has been found that with these initiators, upon irradiation with light, a high through-curing depth can be achieved, without the initiators leading to discolorations. This is a great advantage in many technical and particularly medical materials.

The compounds of general formulae (I) and (I') are particularly suitable for the preparation of dental materials, bone cements and quite particularly of contact lenses, intraocular lenses or other medical shaped parts, such as e.g. ear shells, cartilage implants and artificial tissue parts.

The great through-curing depth upon curing with light in the visible wavelength range is also a substantial advantage in technical applications. The initiators of Formulae (I) and (I') are therefore also suitable for a plurality of non-medical uses, such as for example for the preparation of printing inks or paints, varnishes, adhesives, for the preparation of printing plates, integrated circuits, photoresists, soldering masks, inks for colour printers, as materials for holographic data storage, for the preparation of nanosized microelectromechanical elements, optical waveguides, shaped parts and for the optical preparation of information carriers. A main field of application is use as photoinitiator in the stereolithographic preparation of technical shaped parts, e.g. of precision shaped parts and ceramic green bodies.

The compositions according to the invention preferably contain, relative to the total mass of the composition, 0.001 to 5 wt.-%, particularly preferably 0.01 to 1.0 wt.-% of the acyl germanium compound of Formula (I) or (I'). In addition to the acyl germanium, compound of Formula (I) or (I') the compositions preferably also contain a polymerizable binder. Preferred binders are radically and/or cationically polymerizable monomers and/or prepolymers, particularly preferably radically polymerizable monomers, radically polymerizable prepolymers or a mixture thereof.

Mono- or multifunctional (meth)acrylates or mixtures thereof are particularly suitable as radically polymerizable binders. By monofunctional (meth)acrylic compounds is meant compounds with one, by polyfunctional (meth)acrylates compounds with two or more, preferably 2 to 3, polymerizable groups.

Examples in this respect are methyl, ethyl, hydroxyethyl, butyl, benzyl, tetrahydrofurfuryl or isobornyl (meth)acrylate, bisphenol A di(meth)acrylate, bis-GMA (an addition product of methacrylic acid and bisphenol A diglycidyl ether), UDMA (an addition product of 2-hydroxyethyl methacrylate and 2,2,4-trimethyl hexamethylene diisocyanate), di-, tri- or tetraethylene glycol di(meth)acrylate, trimethylolpropane tri(meth)acrylate, pentaerythritol tetra(meth)acrylate, as well as glycerol di- and tri(meth)acrylate, 1,4-butanediol di(meth)acrylate, 1,10-decanediol di(meth)acrylate or 1,12-dodecanediol di(meth)acrylate. Compositions which contain at least one radically polymerizable monomer with 2 or more, preferably 2 to 3 radically polymerizable groups, are particularly preferred, Polyfunctional monomers have cross-linking properties.

Hydrolytically stable diluting monomers such as hydrolytically stable mono(meth)acrylates can also be used as radically polymerizable binders, e.g. mesitylmethacrylate or 2(alkoxy-methyl)acrylic acids, e.g. 2-(ethoxymethyl)acrylic acid, 2-(hydroxymethyl)acrylic acid, N-mono- or -disubstituted acryl amides, such as e.g. N-ethylacrylamide, N,N-dimethacrylamide, N-(2-hydroxyethyl)acrylamide or N-Methyl-N-(2-hydroxyethyl)acrylamide, or N-monosubstituted methacrylamides, such as e.g. N-ethylmethacrylamide or N-(2-hydroxyethyl)methacrylamide and also N-vinylpyrrolidone or allyl ether. Preferred examples of hydrolytically stable cross-linking monomers are urethanes of 2-(hydroxymethyl)acrylic acid and diisocyanates, such as 2,2,4-trimethylhexamethylene diisocyanate or isophorone diisocyanate; cross-linking pyrrolidones, such as e.g. 1,6-bis(3-vinyl-2-pyrrolidonyl) hexane, or commercially accessible bisacrylamides such as methylene or ethylene bisacrylamide, or bis-(meth) acrylamides, such as e.g. N,N'-diethyl-1,3-bis (acrylamido) propane, 1,3-bis (methacrylamido) propane, 1,4-bis (acrylamido) butane or 1,4-bis(acryloyl) piperazine which can be synthesized by reaction from, the corresponding diamines with (meth) acrylic acid, chloride.

Known low-shrinkage radically ring-opening polymerizable monomers such as e.g. mono- or multifunctional vinyl cyclopropanes or bicylic cyclopropane derivatives (cf, DE 196 16 183 C2 or EP 1 413 569 A1) or cyclic allyl sulphides (cf. U.S. Pat. Nos. 6,043,361 or 6,344,556) can also be used as radically polymerizable binders. These monomers can also be used in combination with the di(meth)acrylate cross-linkers listed above. Suitable ring-opening polymerizable monomers are vinyl cyclopropanes, such as 1,1-di(ethoxycarbonyl)- or 1,1-di(methoxycarbonyl)-2-vinyl cyclopropane or the esters of 1-ethoxycarbonyl- or 1-methoxycarbonyl-2-vinyl cyclopropane carboxylic acid with ethylene glycol, 1,1,1-trimethylolpropane, 1,4-cyclohexanediol or resorcinol. Suitable bicyclic cyclopropane derivatives are 2-(bicyclo[3.1.0]hex-1-yl)acrylic acid methyl or ethyl esters or their derivatives which are disubstituted in 3-position, such as (3,3-bis(ethoxycarbonyl)-bicyclo[3.1.0]hex-1-yl) acrylic acid methyl or ethyl ester.

Suitable cyclic allyl sulphides are the addition products of 2-(hydroxymethyl)-6-methylene-1,4-dithiepane or 7-hydroxy-3-methylene-1,5-dithiacyclooctane with 2,2,4-trimethyl hexa-methylene-1,6-diisocyanate or an asymmetrical hexamethylene diisocyanate trimer (e.g. Desmodur® VP LS 2294 from Bayer AG).

Formulations based on vinyl esters, vinyl carbonates and vinyl carbamates are also preferred as radically polymerizable monomers. In addition, styrene, styrene derivatives or divinyl benzene, unsaturated polyester resins and allyl compounds or radically polymerizable polysiloxanes which cam be prepared from suitable methacrylic silanes such as e.g. 3-(methacryloyloxy)propyltrimethoxysilane, and which are described e.g. in DE 199 03 177 C2 can be used as monomers.

Furthermore, mixtures of the previously named monomers with radically polymerizable, acid-group-containing monomers which are also called adhesive monomers can also be used as radically polymerizable binders. Preferred acid-group-containing monomers are polymerizable carboxylic acids, such as maleic acid, acrylic acid, methacrylic acid, 2-(hydroxylmethyl)acrylic acid, 4-(meth)acryloyloxyethyltrimellitic acid anhydride, 10-methacryloyloxydecylmalonic acid, N-(2-hydroxy-3-metnacryloyloxypropyl)-N-phenylglycine or 4-vinylbenzoic acid.

Radically polymerizable phosphonic acid monomers, in particular vinylphosphonic acid, 4-vinylphenylphosphonic acid, 4-vinlybenzylphosphonic acid, 2-methacryloyloxyethylphosphonic acid, 2-methacrylamidoethylphoshonic acid, 4-methacryl-amido-4-methyl-pentyl-phosphonic acid, 2-[4-(dihydroxylphosphoryl)-2-oxa-butyl]-acrylic acid or 2-[2-dihydroxyphosphoryl)-ethoxymethyl]-acrylic acid ethyl or 2,4,6-trimethyl-phenyl ester are also suitable as adhesive monomers.

Furthermore, acidic polymerizable phosphoric acid esters, in particular 2-methacryloyloxypropyl mono- or dihydrogen phosphate, 2-methacryloyloxyethyl mono- or dihydrogen phosphate, 2-methacryloyloxyethylphenyl hydrogen phosphate, dipentaerythritol-pentamethacryloyloxyphosphate, 10-methacryloyloxydecyl-dihydrogen phosphate, dipentaerythritol-pentamethacryloyloxyphosphate, phosphoric acid mono-(1-acryloyl-piperidine-4-yl)-ester, 6-(methacrylamido)hexyl dihydrogen phosphate and 1,3-bis-(N-acryloyl-N-propyl-amino)-propane-2-yl-dihydrogen phosphate are suitable as adhesive monomers.

In addition, polymerizable sulphonic acids are suitable as adhesive monomers, in particular vinyl sulphonic acid, 4-vinylphenyl sulphonic acid or 3-(methacrylamido)propyl sulphonic acid.

Thiol-ene resins which contain mixtures of mono- or multifunctional mercapto compounds and di- or multifunctional unsaturated monomers, above all allyl or norbornene compounds are particularly suitable as binders curable by polyaddition.

Examples of mono- or multifunctional mercapto compounds are o, m or p-dimercaptobenzene and esters of thioglycol or of 3-mercaptopropionic acid with ethylene, propylene or butylene glycol, hexanediol, glycerol, trimethylolpropane or pentaerythritol.

Examples of di- or multifunctional allyl compounds are esters of allyl alcohol with di- or tricarboxylic acids, such as malonic, maleic, glutaric, succinic, adipic, sebacic, phthalic, terephthalic or gallic acid and mono- or trifunctional allyl ethers, such as e.g. diallyl ether, $\alpha$, $\omega$-bis[allyloxy] alkane, resorcin or hydroquinone diallyl ether and pyrogallol triallyl ether, or other compounds such as e.g. 1,3,5-triallyl-1,3,5-triazine-2,4,6-(1H,3H, 5H)-trione, tetraallylsilane or tetraallylorthosilicate.

Examples of di- or multifunctional norbornene compounds are Diels-Alder addition products of cyclopentadiene or furan with di- or multifunctional (meth) acrylates, as well as esters and urethanes of 5-norbornene-2-methanol or 5-norbornene-2-ol with di- or polycarboxylic acids such as e.g. malonic, maleic, glutaric, succinic, adipic, sebacic, phthalic, terephthalic or gallic acid, with, respectively, di- or polyisocyanates, such as hexametnylene diisocyanate or its cyclic trimer, 2,2,4-trimethylhexamethylene diisocyanate, toluylene diisocyanate or isophorone diisocyanate.

In addition to the acyl germanium compounds of general formula (I) the compositions according to the invention may advantageously also contain known photoinitiators (cf, J. P. Fouassier, J. F. Rabek (eds.), Radiation Curing in Polymer Science and Technology, Vol. II, Elsevier Applied Science, London and New York 1993) for the UV or visible range, such as e.g.: benzoin ethers, dialkyl benzil ketals, dialkoxyacetophenones, acyl or bisacyl phosphine oxides, $\alpha$-diketones such as 9,10-phenanthrenequinone, diacetyl, furil, anisil, 4,4'-dichlorobenzil and 4,4'-dialkoxybenzil and camphorquinone.

For dual curing the compositions according to the invention can also contain, in addition to the tetraacylgermanes of general formula (I) and/or the $(acyl)_k$ $(alkyl)_{4-k}$ germanes of Formula I', azo compounds such as 2,2'-azobis(isobutyronitrile) (AIBN) or azobis-(4-cyano valeric acid), or peroxides, such as dibenzoyl peroxide, dilauroyl peroxide, tert-butylperoctoate, tert-butylperbenzoate or di-(tert-butyl)-peroxide. To accelerate initiation by means of peroxides, combinations with aromatic amines can also be used. Redox systems which have already proved worthwhile are: combinations of benzoylperoxide with amines such as N,N-dimethyl-p-toluidine, N, N-dihydroxyethyl-p-toluidine, p-dimetnylaminobenzoic acid ethyl ester or structurally related systems. In addition, redox systems consisting of peroxides and reducing agents such as e.g. ascorbic acid, barbiturates or sulphinic acids or combinations of hydroperoxides with reducing agents and catalytic metal ions, such as e.g. a mixture of cumene hydroperoxide, thiourea derivative and copper(II)-acetyl acetonate, are also suitable for dual curing.

According to the invention compositions are preferred which contain one or more fillers, preferably organic or inorganic particulate fillers. Preferred inorganic particulate fillers are amorphous spherical nanoparticulate fillers based on oxides such as pyrogenic silicic acid or precipitated silicic acid, $ZrO_2$ and $TiO_2$ or mixed oxides of $SiO_2$, $ZrO_2$ and/or $TiO_2$ with an average particle diameter of from 10 to 200 nm, mini fillers such as quartz, glass ceramic or glass powder with an average particle size of from 0.2 to 5 µm and x-ray opaque fillers such as ytterbium trifluoride or nanoparticulate tantalum(V) oxide or barium sulphate. In addition, fibrous fillers such as nanofibres, glass fibres, polyamide or carbon fibres can also be used.

For non-dental uses, in addition to the above-named materials, homo- and/or copolymers, preferably poly((meth)

acrylate)s, vinyl polymers, preferably polystyrene or polyvinyl acetate, or condensation polymers, preferably polyester, are suitable as fillers. These fillers are preferably used as powder with an average particle size between 0.5 and 100 μm. They are partially soluble in the monomer.

Additionally, the compositions according to the invention can, if necessary, contain further additives such as e.g. stabilizers, UV absorbers, dyes or pigments and solvents, such as e.g. water, ethanol, acetone and/or ethyl acetate or slip additives.

The materials according to the invention preferably contain:
(a) 0.001 to 5 wt.-% tetraacyl germane (s) of general formula (I),
(b) 10 to 99.9 wt.-% radically polymerizable binder,
(c) 0 to 85 wt.-% filler and optionally
(d) 0 to 70 wt.-% additive(s).

Unless otherwise indicated, all percentages relate to the total mass of the material.

Materials which are particularly suitable as dental cements preferably contain:
(a) 0.001 to 5 wt.-% tetraacyl germane (s) of general formula (I),
(b) 10 to 50 wt.-% radically polymerizable binder,
(c) 40 to 70 wt.-% filler and
(d) 0 to 5 wt.-% additive.

Materials which are particularly suitable as dental composites preferably contain:
(a) 0.001 to 5 wt.-% tetraacyl germane(s) of general formula (I),
(b) 10 to 40 wt.-% radically polymerizable binder,
(c) 50 to 70 wt.-% filler and
(d) 0 to 5 wt.-% additive(s).

Materials which are particularly suitable as dental coating materials preferably contain:
(a) 0.001 to 5 wt.-% tetraacyl germane(s) of general formula (I),
(b) 20 to 99.9 wt.-% radically polymerizable binder,
(c) 0 to 20 wt.-% nanoparticulate fillers and
(d) 0.01 to 2 wt.-% additive(s),
(e) 0 to 70 wt.-% solvent.

Materials which are particularly suitable as dental adhesives preferably contain:
(a) 0.001 to 5 wt.-% tetraacyl germane (s) of general formula (I),
(b) 20 to 98.99 wt.-% radically polymerizable binder,
(c) 0 to 20 wt.-% nanoparticulate fillers
(d) 0.01 to 2 wt.-% additive,
(e) 0 to 50 wt.-% solvent and
(f) 1 to 20 wt.-% radically polymerizable adhesive monomers.

Materials for dental prostheses or surgical moulded bodies preferably contain:
(a) 0.001 to 5 wt.-% tetraacyl germane(s) of general formula (I),
(b) 30 to 99.9 wt.-% radically polymerizable binder,
(c) 0 to 60 wt.-% filler(s) and optionally
(d) 0 to 3 wt.-% additive(s).

Materials for plastic shaped parts preferably contain:
(a) 0.001 to 5 wt.-% tetraacyl germane(s) of general formula (I),
(b) 30 to 99.9 wt.-% radically polymerizable binder,
(c) 0 to 60 wt.-% filler and optionally
(d) 0 to 15 wt.-% additive(s).

Materials for ceramic green bodies preferably contain:
(a) 0.001 to 5 wt.-% tetraacyl germane (s) of general formula (I),
(b) 0 to 40 wt.-% radically polymerizable binder,
(c) 40 to 90 wt.-% filler and optionally
(d) 0 to 20 wt.-% additive (s), The materials according to the invention which contain tetraacyl germanes of general formula (I) as photoinitiator, can be used for the preparation of photopolymerizates, composites, cements, coating materials, primers or adhesives. They are particularly suitable for uses in the medical field, above all for the preparation of dental materials, such as filling composites, fixing cements, adhesives, prosthesis materials, veneering materials, crowns or inlays or coatings.

The dental materials are suitable primarily for intraoral application by the dentist to restore damaged teeth, i.e. for therapeutic application, e.g. as dental cements, filling composites and veneering materials. However, they can also be used extraorally, for example in the manufacture or repair of dental restorations, such as prostheses, artificial teeth, inlays, onlays, crowns and bridges.

Furthermore, the materials according to the invention are suitable for medical use in surgery, e.g. in tissue regeneration, for the preparation of hearing aids or in ophthalmology for the preparation of intraocular lenses or contact lenses.

In technical applications the tetraacyl germanes of general formula (I) can be used as photoinitiator in stereolithography or in 3D printing for the preparation of moulded bodies, prototypes or green bodies, in the field of coatings or in microelectronics e.g. in photoresist technology.

The invention is described in further detail in the following with reference to examples.

Example 1

Synthesis of Tetrabenzoyl Germane (TBGe)

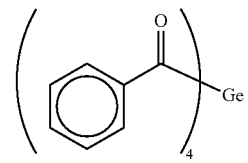

a) Synthesis of tetrakis(trimethylsilyl)germane [(Me$_3$Si)$_4$Ge]

10.00 g (1.4 mol) lithium was placed in a flask with a dropping funnel and pressure equalizer, and 300 mL dry THF was added. Trimethylchlorosilane (95 ml, 0.75 mol) was rapidly added dropwise and stirred for 10 min. at −78° C. Germanium tetrachloride (21 ml, 0.19 mol, 1:5 diluted in THF) was then added very slowly dropwise at −78° C. (ca. 2 h). Once the addition had ended the reaction solution was heated to room temperature and stirred for a further 12 hours. For working up the reaction mixture was first filtered through Celite and then poured onto 1 M H$_2$SO$_4$/ice. After phase separation in the dropping funnel the aqueous phase was extracted 3 times with diethylether, the combined organic phases were dried over anhydrous Na$_2$SO$_4$, filtered and the solvent was removed in a rotavapor. For purification the crude product was sublimated (p<5 mbar; T>150° C.). The yield after sublimation was 26.8 g (Me$_3$Si)$_4$Ge (42%).

NMR spectroscopy: $^1$H(CDCl$_3$) δ[ppm]=0.24 (s, Si(CH$_3$)$_3$). $^{29}$Si (CDCl$_3$): δ[ppm]=−5.33 (SiMe$_3$).

b) Synthesis of tetrabenzoyl germane (TBGe)

3.00 g (8.21 mmol; 1.00 eq.) Tetrakistrimethylsilyl germane and 1.01 g KOtBu (9.03 mmol; 1.1 eq.) were weighed into a Schlenk flask and dissolved in 20 ml ethylene glycol dimethyl ether (DME). The reaction was complete when the reaction solution had a clear yellow to orange colour. After approximately one hour 4.18 g (33.66 mmol, 4.1 eq.) benzoyl fluoride was added by means of a syringe. The reaction solution became black and, after the addition was complete, orange. The reaction solution was then stirred overnight at room temperature. After aqueous working up with 3% $H_2SO_4$ the phases were separated and the aqueous phase extracted 3 times with diethyl ether. The combined organic phases were dried over anhydrous sodium sulphate and the volatile components removed in a rotary evaporator. The obtained crude product was recrystallized from acetone and 1.70 g pure tetrabenzoyl germane (42%) was obtained as a crystalline, yellow solid (melting point: 82.5-83.0° C.).

NMR spectroscopy: $^1H$ (CDCl$_3$): δ[ppm]=7.99-7.96 (m, 2H, aryl-H), 6.84-6.82 (m, 3H, aryl-H). $^{13}C$ (CDCl$_3$): δ[ppm]= 222.01 (GeCOPh), 140.57 (aryl-C1), 133.81 (aryl-C2), 129.15 (aryl-C3), 128.77 (aryl-C4).

UV-VIS spectroscopy: λ[nm](ε [L mol$^{-1}$ cm$^{-1}$])=403 (1240), 419sh (1050).

IR spectroscopy: ν [cm$^{-1}$]=1639, 1617 (m, νC=O); 1590, 1574, 1444 (m, νC=C); 880, 762, 673 (s, δC—H).

Example 2

Synthesis of tetrakis(2,4,6-trimethylbenzoyl)germane (TMGe)

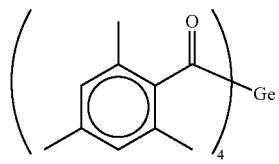

2.77 g (7.66 mmol; 1.00 eq.) (Me$_3$Si)$_4$Ge and 0.94 g KOtBu (8.4 mmol; 1.1 eq.) were weighed into a Schlenk vessel and dissolved in 15 ml DME. The reaction was complete when the reaction solution had a clear yellow to orange colour. After approximately one hour the obtained solution was slowly added dropwise to a solution, cooled to −78° C., of 1.66 g (0.91 mmol, 1.2 eq.) 2,4,6-trimethylbenzoyl chloride in 80 ml diethyl ether and the obtained mixture stirred overnight at room temperature. After aqueous working up with 3% $H_2SO_4$ the phases were separated and the aqueous phase extracted 3 times with diethyl ether. The combined organic phases were dried over anhydrous sodium sulphate and the volatile components removed in a rotary evaporator. The formed crude product with a mass of 3.85 g contained 36% tetraacyl germanium and 64% monoacyl germanium compound and was separated by column chromatography over silica gel (gradient: heptane, toluene). Recrystallization from acetone was then carried out, and 1.58 g (24%) tetrakis(2,4,6-trimethylbenzoyl)germane was obtained as a crystalline, yellow solid (melting point: 198-199° C.).

NMR spectroscopy: $^1H$ (CDCl$_3$): δ[ppm]=6.57 (s, 2H, Aryl-H), 2.24 (s, 3H, para-CH$_3$), 2.06 (s, 6H, ortho-CH$_3$). $^{13}C$ (CDCl$_3$): δ[ppm]=233.40 (GeCOMes), 141.60 (aryl-C1), 139.26 (aryl-C2), 132.88 (aryl-C3), 128.53 (aryl-C4), 21.15 (para-CH$_3$), 19.13 (ortho-CH$_3$).

UV-VIS spectroscopy: λ[nm](ε[L mol$^{-1}$ cm$^{-1}$])=288 (17428), 376 (1475).

IR spectroscopy: ν[cm$^{-1}$]=2917 (w, ν$_{as}$CH$_3$); 1639, 1608 (m, νC=O); 1202 (m, δ$_{as}$CH$_3$); 833, 609 (m, ρCH$_3$).

Example 3

Preparation of Light-Curing Resins Using Tetrabenzoyl Germane (TBGe) or tetrakis(2,4,6-trimethylbenzoyl)germane (TMGe) from Examples 1 and 2

Various light-curing resin systems were prepared from a mixture (values given in mass-%) of dimethacrylates Bis-GMA (addition product of methacrylic acid and bisphenol-A-diglycidyl ether)), UDMA (addition product of 2-hydroxyethyl methacrylate and 2,2,4-trimethyl hexamethylene diisocyanate) and D$_3$MA (decanediol-1,10-dimethacrylate) and the Ge initiators tetrabenzoyl germane (TBGe), tetrakis (2,4,6-trimethyl benzoyl)germane (TMGe) and dibenzoyl diethyl germane (DBEGe, as reference) (Table 1). The resin systems R1 and R4 (0.29 mmol/100 g) or R2, R3 and R5 (0.59 mmol/100 g) contain the same molar quantity of photoinitiator.

TABLE 1

Composition of resins R1 to R5

| | Resin | | | | |
|---|---|---|---|---|---|
| Component | R1 | R2 | R3 | R4* | R5* |
| TBGe | 0.14 | 0.29 | — | — | — |
| TMGe | — | — | 0.39 | — | — |
| DBEGe | — | — | — | 0.10 | 0.20 |
| Bis-GMA | 42.10 | 42.10 | 42.10 | 42.10 | 42.10 |
| UDMA | 37.46 | 37.31 | 37.21 | 37.50 | 37.40 |
| D$_3$MA | 20.30 | 20.30 | 20.30 | 20.30 | 20.30 |

*Comparison example

Test pieces were prepared from the materials, which were irradiated twice for 3 minutes with a dental light source (Spectramat®, Ivoclar Vivadent AG) and thereby cured. The flexural strength and the flexural modulus of elasticity were determined according to ISO standard ISO4049 (Dentistry—Polymer-based filling, restorative and luting materials) after 24 h storage of the test pieces at room, temperature (RT) or after 24 h storage in water (WS) at 37° C. (Table 2).

TABLE 2

Flexural strength (FS, MPa) and flexural modulus of elasticity (FME, GPa) of polymerized resins R1 to R5

| | R1 | R2 | R3 | R4* | R5* |
|---|---|---|---|---|---|
| FS, RT | 72.7 ± 3.5 | 81.7 ± 9.5 | 81.5 ± 5.5 | 58.5 ± 2.3 | 79.7 ± 7.5 |
| FS, WS | 98.2 ± 8.7 | 115.2 ± 11.2 | 101.8 ± 6.1 | 75.3 ± 3.0 | 96.4 ± 8.1 |

TABLE 2-continued

Flexural strength (FS, MPa) and flexural modulus of elasticity (FME, GPa) of polymerized resins R1 to R5

|  | R1 | R2 | R3 | R4* | R5* |
|---|---|---|---|---|---|
| FME, RT | 1.59 ± 0.12 | 2.25 ± 0.22 | 1.89 ± 0.21 | 1.15 ± 0.07 | 1.76 ± 0.19 |
| FME, WS | 1.15 ± 0.20 | 2.48 ± 0.10 | 2.37 ± 0.12 | 1.54 ± 0.11 | 2.19 ± 0.20 |

*Comparison example

The results in Table 2 prove that the resins R1 and R3 with the tetra(benzoyl)germane TBGe according to the invention as photoinitiator in comparison with the reference resins R4 and R5 based on the known di(benzoyl)germane DBEGe with the same molar concentration of the photoinitiators (compare R1 with R4 or R2 with R5) lead to photopolymerisates with improved strength, and a higher modulus of elasticity.

Example 4

Preparation of Light-Curing Resins Using Tetrabenzoyl Germane (TBGe) or tetrakis(2,4,6trimethylbenzoyl)germane (TMGe) from Examples 1 and 2

The composite pastes K1 to K5 were prepared from the resins R1 to R5 from Example 3 by means of a roll mill ("Exakt" model, Exakt Apparatebau, Norderstedt). In each case 36.44 wt. % of resins R1 to R5 were filled with 52.22 wt. % of silanized glass filler GM 27884 (1.0 μm, Schott), 4.02 wt. % of silanized glass filler GM G018-056 (1.0 μm, Schott), 4.02 wt. % silanized $SiO_2$—$ZrO_2$ mixed oxide Spherosil (Transparent Materials, USA) 0.80 wt. % of silanized pyrogenic silicic acid OX-50 (Degussa) and 2.50 wt. % ytterbium trifluoride $YbF_3$ (Sukgyung, South Korea). Analogous to Example 3, test pieces were prepared from the pastes, cured, and the flexural strength and the elastic modulus determined (Table 3).

TABLE 3

Flexural strength (FS, MPa) and flexural modulus of elasticity (FME, GPa) of the polymerized composite pastes K1 to K5

|  | K1 | K2 | K3 | K4* | K5* |
|---|---|---|---|---|---|
| FS, RT | 96.5 ± 9.2 | 125.4 ± 7.7 | 114.8 ± 4.6 | 92.4 ± 6.4 | 112 ± 6.9 |
| FS, WS | 117.4 ± 8.7 | 129.7 ± 9.9 | 133.8 ± 4.8 | 101.9 ± 9.0 | 123.3 ± 3.5 |
| FME, RT | 5.51 ± 0.33 | 7.13 ± 0.40 | 6.73 ± 0.37 | 4.99 ± 0.39 | 6.20 ± 0.32 |
| FME, WS | 6.16 ± 0.46 | 7.68 ± 0.87 | 7.36 ± 0.62 | 5.45 ± 0.64 | 6.59 ± 0.34 |

*Comparison example

The results in Table 3 prove that the composite pastes K1 and K3 with the tetra(benzoyl)germane TBGe according to the invention as photoinitiator in comparison with the reference pastes K4 and K5 based on the known di(benzoyl) germane DBEGe with the same molar concentration of the photoinitiators (compare K1 with K4 or K2 with K5) after curing, lead to composites with an improved strength and higher modulus of elasticity.

The invention claimed is:

1. Acyl germanium compound according to general formula (I),

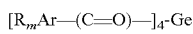
$[R_m Ar—(C═O)—]_4$-Ge   (I)

in which the variables have the following meanings:
Ar a mono- or polycyclic hydrocarbon radical with 6 to 18 ring-carbon atoms, which can be substituted m times by the R group and which can contain one or more heteroatoms in the ring, wherein
m is an integer from 0 to 6 and cannot be greater than the number of substitutable hydrogen atoms in Ar,
R is halogen, $NR^1_2$, OH, $OSiR^2_3$, (C═O)$R^3$, CN, $NO_2$, $CF_3$, $COOR^4$, or a $C_1$- to $C_{20}$-alkyl, -alkenyl, -alkoxy or -alkenoxy radical, which can be linear, branched or cyclic, which can be interrupted by one or more O atoms and which can contain a radically polymerizable group, or ═O, wherein
$R^1$-$R^3$ independently of each other are in each case H or a linear or branched $C_1$- to $C_{12}$-alkyl radical and
$R^4$ is H, a linear or branched $C_1$- to $C_{12}$-alkyl radical or $SiR^5_3$, wherein
$R^5$ is a linear or branched $C_1$- to $C_{10}$-alkyl radical.

2. Acyl germanium compound according to claim 1, in which the variables have the following meanings:
Ar an aromatic $C_6$-$C_{10}$ radical, which can be substituted m times by R, wherein
m is an integer from 1 to 3 and
R is Cl, $NR^1_2$, $OSiR^2_3$, (C═O) $R^3$, CN, $NO_2$, $CF_3$, $COOR^4$, or a $C_1$- to $C_{10}$-alkyl, -alkenyl, -alkoxy or -alkenoxy radical, which can be linear, branched or cyclic, which can be interrupted by one or more O atoms, and which can contain a radically polymerizable group, wherein
$R^1$-$R^3$ independently of each other are in each case H or a linear or branched $C_1$- to $C_8$-alkyl radical and
$R^4$ is H, a linear or branched $C_1$- to $C_8$-alkyl radical or $SiR^{10}_3$ and
$R^5$ is a linear or branched $C_1$ to $C_5$ alkyl radical.

3. Acyl germanium compound according to claim 1, in which the variables have the following meanings:
Ar a phenyl radical, pyridyl radical, naphthyl radical, anthryl radical, anthraquinone-yl radical, which can be substituted m times by R, wherein
m is an integer from 1 to 3 and
R is $NR^1_2$, CN, $NO_2$, $CF_3$, a $C_1$- to $C_3$-alkyl radical or $C_1$- to $C_3$-alkoxy radical, wherein
$R^1$ is H or a linear $C_1$- to $C_3$-alkyl radical.

4. Composition which, relative to its total mass contains 0.001 to 5 wt. % of an acyl germanium compound of Formula (I) according to claim 1 and at least one polymerizable binder.

5. Composition according to claim 4 which contains as polymerizable binder at least one radically polymerizable monomer and/or prepolymer.

6. Composition according to claim 5, which contains as binder at least one mono- or multifunctional (meth)acrylate or a mixture thereof.

7. Composition according to claim 4, which contains
0.001-5 wt. % acyl germanium compound of Formula (I),
10 to 99.9 wt.-% polymerizable binder,
0 to 85 wt.-% filler, relative in each case to the total mass of the composition.

8. Process of using an acyl germane according to Formula (I) as initiator for radical polymerization, wherein Formula (I) comprises

$$[R_mAr-(C=O)-]_4-Ge \qquad (I)$$

in which the variables have the following meanings:
Ar a mono- or polycyclic hydrocarbon radical with 6 to 18 ring-carbon atoms, which can be substituted m times by the R group and which can contain one or more heteroatoms in the ring, wherein
m is an integer from 0 to 6 and cannot be greater than the number of substitutable hydrogen atoms in Ar,
R is halogen, $NR^1_2$, OH, $OSiR^2_3$, $(C=O)R^3$, CN, NO, $CF_3$, $COOR^4$, or a $C_1$- to $C_{20}$-alkyl, -alkenyl, -alkoxy or -alkenoxy radical, which can be linear, branched or cyclic, which can be interrupted by one or more O atoms and which can contain a radically polymerizable group, or =O, wherein
$R^1$-$R^3$ independently of each other are in each case H or a linear or branched $C_1$- to $C_{12}$-alkyl radical and
$R^4$ is H, a linear or branched $C_1$- to $C_{12}$-alkyl radical or $SiR^5_3$, wherein
$R^5$ is a linear or branched $C_1$- to $C_{10}$-alkyl radical.

9. Acyl germanium compound according to claim 2, wherein the radically polymerizable group comprises vinyl, methacrylate, (meth)acrylamide or N-alkylacrylamide, and wherein the radically polymerizable group in the case of non-cyclic radicals is terminal.

10. Acyl germanium compound according to claim 3, wherein R is linear and can bear a terminal radically polymerizable group comprising vinyl, acrylate, methacrylate.

* * * * *